(12) United States Patent  (10) Patent No.: US 8,466,475 B2
Ichimura et al.  (45) Date of Patent: Jun. 18, 2013

(54) LIGHT DETECTING CHIP AND LIGHT DETECTING DEVICE PROVIDED WITH LIGHT DETECTING CHIP

(75) Inventors: Isao Ichimura, Tokyo (JP); Masanobu Yamamoto, Kanagawa (JP); Shinichi Kai, Tokyo (JP)

(73) Assignee: Sony Corporation, Tokyo (JP)

( * ) Notice: Subject to any disclaimer, the term of this patent is extended or adjusted under 35 U.S.C. 154(b) by 128 days.

(21) Appl. No.: 12/846,485

(22) Filed: Jul. 29, 2010

(65) Prior Publication Data

US 2011/0037077 A1 Feb. 17, 2011

(30) Foreign Application Priority Data

Aug. 12, 2009 (JP) ................. P2009-187313

(51) Int. Cl.
*H01L 31/153* (2006.01)
(52) U.S. Cl.
USPC ..................... 257/84; 257/E31.096
(58) Field of Classification Search
CPC ........ H01L 25/167; H01L 27/15; H01L 31/173
USPC .............. 257/84, 432, E31.096; 250/458.1, 250/200, 216; 356/72, 73, 446; 435/283.1, 435/287.1, 288.04
See application file for complete search history.

(56) References Cited

U.S. PATENT DOCUMENTS

| 5,636,015 | A  | * | 6/1997  | Imura et al. ................. 356/72 |
| 7,427,509 | B2 |   | 9/2008  | Yang et al. |
| 2002/0182716 | A1 |   | 12/2002 | Weisbuch et al. |
| 2004/0155927 | A1 | * | 8/2004  | Nakao et al. ................. 347/54 |
| 2005/0051733 | A1 |   | 3/2005  | Wiki et al. |
| 2006/0023216 | A1 |   | 2/2006  | Labeye et al. |
| 2006/0028642 | A1 |   | 2/2006  | Weisbuch |
| 2008/0153155 | A1 |   | 6/2008  | Kato et al. |
| 2008/0245971 | A1 |   | 10/2008 | Wimberger-Friedl et al. |
| 2009/0009756 | A1 | * | 1/2009  | Yamamichi et al. .......... 356/246 |

FOREIGN PATENT DOCUMENTS

| JP | 2007-139744 | 6/2007 |
| JP | 2007-187582 | 7/2007 |
| JP | 2008-015770 | 1/2008 |
| JP | 2008-17779 | 1/2008 |
| WO | WO 01/03833 | 1/2001 |

OTHER PUBLICATIONS

Fink, "Types of Anti-Reflective Treatments and When to Use Them", 2009, at www.photonicsonline.com, pp. 28-31, Jan. 20, 2009.*
European Search Report dated May 9, 2012 corresponding to European Application No. 10008106.6.

* cited by examiner

*Primary Examiner* — Nikolay Yushin
(74) *Attorney, Agent, or Firm* — K&L Gates LLP

(57) ABSTRACT

A light detecting chip includes at least one detection region configured to accommodate a sample that is capable of emitting fluorescent light, and a light reflecting section configured to reflect at least a portion of the fluorescent light emitted from the sample in a direction toward a light detector.

19 Claims, 8 Drawing Sheets

LIGHT DETECTING CHIP AND LIGHT DETECTING DEVICE PROVIDED WITH LIGHT DETECTING CHIP

CROSS REFERENCES TO RELATED APPLICATIONS

The present application claims priority to Japanese Patent Application JP 2009-187313 filed on Aug. 12, 2009, the entire content of which is hereby incorporated by reference.

BACKGROUND

The present disclosure relates to a light detecting chip. More particularly, the present disclosure relates to a light detecting chip and a light detecting device provided with the light detecting chip, which are used for analysis of gene expression, examination of infectious disease, gene analysis (such as SNP analysis), protein analysis, and cell analysis.

Comprehensive research and development on gene analysis, protein analysis, and cell analysis are going on in various fields including medical service, innovative drug development, clinical laboratory test, food industry, agriculture, engineering, legal medicine, and criminal identification. Conspicuous among them is a new technology of "lab-on-chip" which permits various reactions (for detection and analysis of nucleic acids, proteins, and cells) to take place in a channel or well of micro scale formed in a chip. It is now attracting attention because of its potential capacity for measuring biomolecules in a simple way.

The problem with the lab-on-chip technology is that mixing, reaction, separation, purification, and detection have to be carried out with an extremely small amount of sample in the channel or well of micro scale formed in a chip. For efficient detection and analysis, it is necessary to contrive good ways and means for chip design and their implementation.

For example, there is proposed in Japanese Patent Laid-open No. 2008-015770 (Patent Document 1) a chip with a micro channel formed therein. This chip is designed such that a reagent mixed with a thermally fusible binder is supported at a prescribed position in the micro channel. After introduction of a sample solution, the chip is heated so that the thermally fusible binder begins to melt at the position where it is supported. This leads to efficient dissolution and mixing and permits the subsequent reaction and analysis to take place at the same position. The result is that it is possible to reduce the number of spots for reaction in the micro channel, which leads to size reduction and cost reduction.

There is proposed in Japanese Patent Laid-open No. 2007-139744 (Patent Document 2) a fluorescence polarization assay which is capable of analysis with a very small amount of sample (about one-hundredth the amount used in the assay in the related art). The assay includes (1) a step of preparing fluorescent probe molecules and biomolecules, (2) a step of injecting them into the micro channel of a Lab-on-a-chip, thereby forming their complex, (3) a step of directing a beam of polarized light to the complex and measuring fluorescent polarization caused by the complex, and (4) a step of quantifying the fluorescent polarization and determining the degree of fluorescent polarization.

There is proposed in Japanese Patent Laid-open No. 2008-17779 (Patent Document 3) a Lab-on-chip which is composed of the following units arranged on a single substrate. A unit for preparation of nucleic acid, which is provided with a first electrode; a unit for introduction of a sample fluid into the nucleic acid preparing unit; a reaction unit communicating with the nucleic acid preparing unit through a channel, the reaction unit being provided with a second electrode; a unit for introduction of drug solution into the reaction unit; a unit for discharge of fluid from the reaction unit; a control circuit connected to the first and second electrodes; and a detecting circuit connected to the second electrode. This Lab-on-chip is capable of replication, synthesis, reaction, and detection of nucleic acids on a single substrate.

There is proposed in Japanese Patent Laid-open No. 2007-187582 (Patent Document 4) a biochip which is provided with detectors (such as working electrode, reference electrode, and counter electrode) and thin-film transistors. This biochip will find use as a biosensing device which is light, thin, short, small, and cheap and yet capable of high performance. It can also be detachably mounted on a biosensor provided with an ink jet head.

SUMMARY

A common way of analyzing a sample is by detection of light (particularly fluorescence) emitted from a sample introduced into a Lab-on-chip upon irradiation with light. It is still an important factor in the field of Lab-on-chip technology to efficiently detect light from an extremely small amount of sample, although many improvements and refinements have been made as mentioned above for more accurate analysis.

However, there are many instances which involve difficulties in efficient detection of light from an extremely small amount of sample because light (such as fluorescence) from a sample diverges in all directions (360°). Moreover, this situation is aggravated more by excitation light and self-emitting fluorescence from any substance contained in the sample, so that efficient detection of desired fluorescence alone is difficult. In fact, an ordinary optical detector can detect about 5% of fluorescence emitted from a sample.

It is a desired to provide a new technology capable of efficient detection of light emitted from a very small amount of sample. The present embodiments enable efficient detection of light from a very small amount of sample by modifying the structure of the chip used for light detection.

In an embodiment, a light detecting chip includes at least one detection region configured to accommodate a sample that is capable of emitting fluorescent light, and a light reflecting section configured to reflect at least a portion of the fluorescent light emitted from the sample in a direction toward a light detector.

In another embodiment, a light detecting device includes a light source configured to emit excitation light, at least one detection region configured to accommodate a sample capable of emitting fluorescent light, a light reflecting section configured to reflect at least a portion of the fluorescent light emitted from the sample in a direction toward a light detector, and a light detection section configured to receive at least a portion of the fluorescent light that is reflected by the light reflecting section.

The light reflecting section of the light detecting chips of the embodiments are not specifically restricted in shape. The light reflecting section may have, for example, a concave shape, a convex shape, or a planar shape.

The light detecting chip according to an embodiment may additionally have light transmission controlling section which blocks light being directed to the sample and transmits fluorescence emitted from the sample.

Owing to the structure of the embodiments, the light detecting chips are capable of reflecting that portion of fluorescence emitted from a sample which is scattered in the direction opposite to the direction in which fluorescence is detected. Therefore, it is capable of efficiently detecting light emitted from a very small amount of sample, and it contributes to improvement in the accuracy of analysis.

Additional features and advantages are described herein, and will be apparent from the following Detailed Description and the figures.

DETAILED DESCRIPTION

Figure 1:
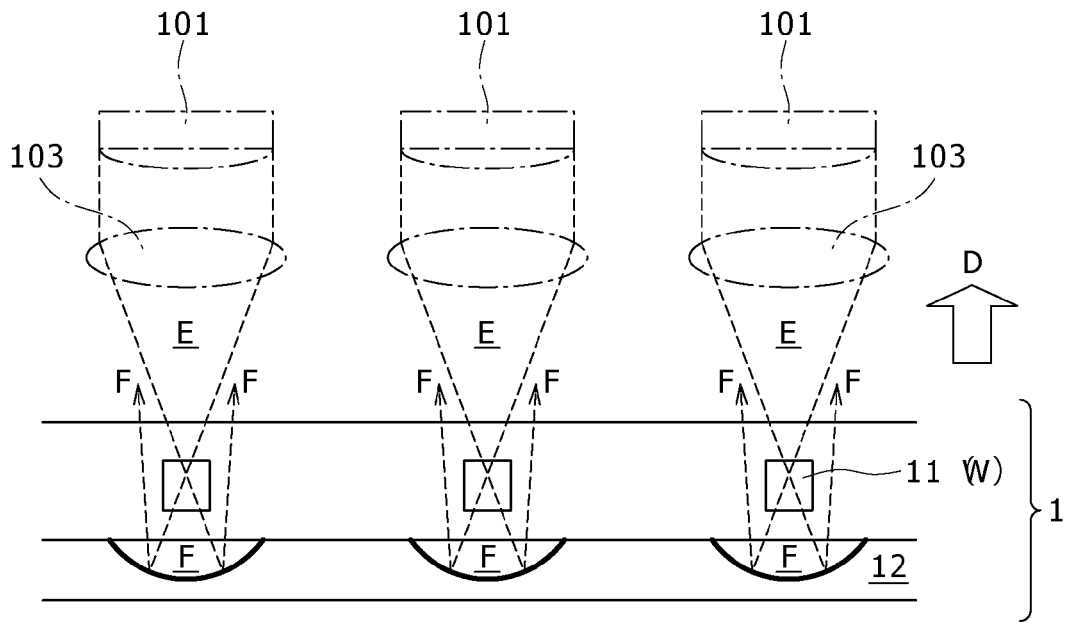
FIG. 1 is a schematic sectional view showing the light detecting chip according to the first embodiment.

Embodiments will be described below with reference to the accompanying drawings. The description below is divided into sections as follows.
1. Light detecting chip 1
   (1) Detection region 11
   (2) Light reflecting section 12
   (3) Light transmission controlling section 13
2. Light detecting device 10
   (1) Light irradiating section 101
   (2) Light detecting section 102
   (3) Condenser lenses 103a and 103b
   (4) Optical filters 104a and 104b
   (5) Apertures 105a, 105b, barrier
1. Light Detecting Chip 1

FIG. 1 is a schematic sectional view showing the light detecting chip 1 according to the first embodiment. The light detecting chip 1 has at least (1) detection region 11 and (2) light reflecting section 12. It may optionally have (3) light transmission controlling section 13 according to need.

The light detecting chip 1 according to an embodiment will be formed from any material which is not specifically restricted. An adequate material is one which is commonly used for bioassay chips capable of light detection. Desirable materials include glass and transparent plastics such as polycarbonate, polyolefin, cycloolefin, acrylic, and silicon resins such as polydimethylsiloxane (PDMS), which are suitable for light detection.

The light detecting chip 1 has several sections as described below into detail.

(1) Detection Region 11

Figure 2:
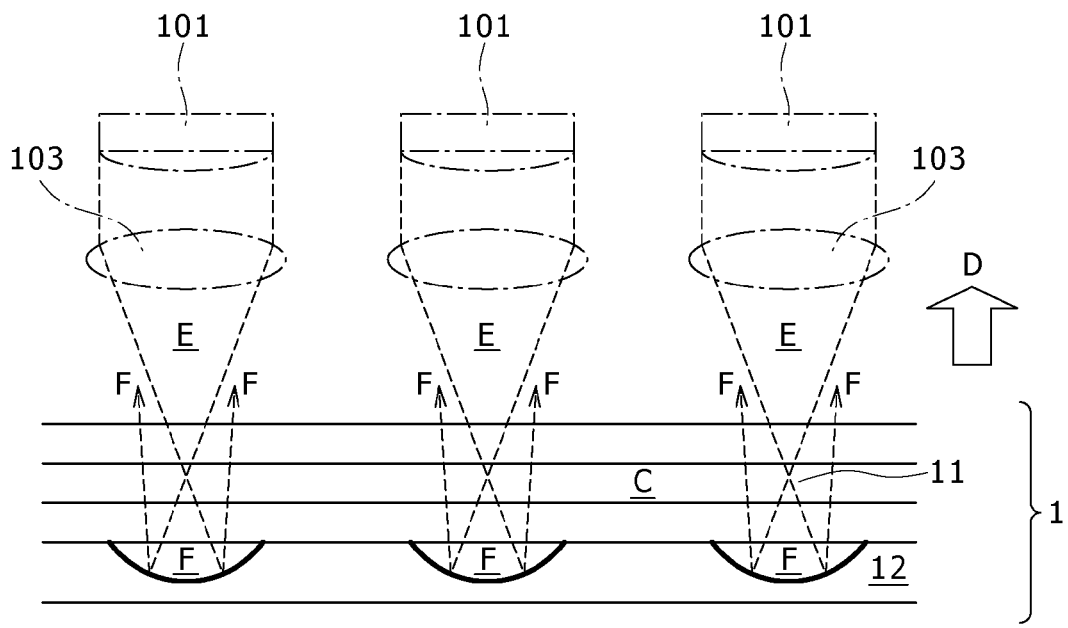
FIG. 2 is a schematic sectional view showing the light detecting chip according to the second embodiment.

The detection region 11 is where there exists a sample to be analyzed and the sample is irradiated with excitation light E and fluorescence F emitted from the sample is detected. The detection region 11 is not specifically restricted in its structure so long as it permits detection of fluorescence F which is emitted from the sample by irradiation with excitation light E. It may be placed in the well W as shown in FIG. 1 for the first embodiment. The detection region 11 may also be placed in the channel C as shown in FIG. 2 for the second embodiment. Incidentally, the second embodiment shown in FIG. 2 is designed such that there are a plurality of detection regions 11 in the channel C. However, it may be modified such that there exists one detection region 11 in one channel C.

Figure 3:
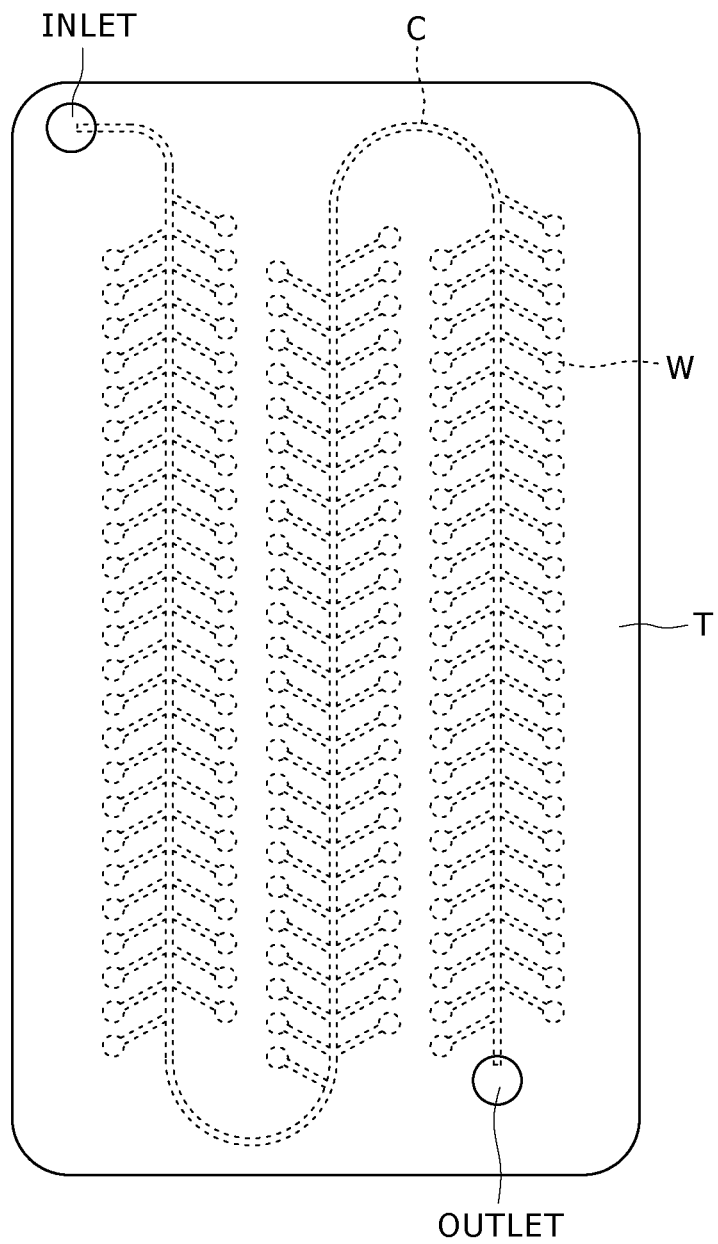
FIG. 3 is a schematic sectional view showing the light detecting chip according to the third embodiment.

Another possibility is that a plurality of detection regions 11 (not shown) are placed in the channel C and the wells W which are formed together in the substrate T as shown in FIG. 3 for the third embodiment.

In the case where the detection region 11 is placed in the channel C, the channel C is not specifically restricted in its width, depth, and cross section. For example, a microchannel having a width smaller than 1 mm can be used for the light detecting chip 1 according to an embodiment.

The detection region 11 may function not only as a site for fluorescence detection but also as a site for amplification of nucleic acid, hybridization, and reaction among nucleic acids, proteins, and cells. In the case where the detection region 11 is placed in the channel C as shown in FIG. 2 for the second embodiment, the process may proceed in such a way that the sample moves through the channel C while undergoing various reactions and the sample which has reached a prescribed position is examined for fluorescence. Moreover, in the case where the channel C and the wells W are formed together in the substrate T as shown in FIG. 3 for the third embodiment, the process may proceed in such a way that the sample moves through the channel C while undergoing various reactions and the sample which has reached a prescribed well W is examined for fluorescence. Alternatively, the process may proceed in such a way that the sample undergoes reactions in each well W and the sample moving through the channel C is examined for fluorescence.

Incidentally, introduction of a sample into each detection region 11 may be accomplished in any known way without specific restrictions. For example, in the third embodiment shown in FIG. 3, the wells W and the channel C connected to them are formed on the substrate T so that the sample is introduced to each detection region 11 (not shown) through the channel C.

(2) Light Reflecting Section 12

The light reflecting section 12 is intended for reflection of fluorescence F emitted from the sample. It is placed at a position where the fluorescence is reflected back to the detection region 11 (in the direction D for fluorescence detection).

Since the sample emits fluorescence F in all directions (360°), fluorescence emitted in the direction opposite to the direction D for fluorescence detection is scattered without being detected. For this reason, the chip in the related art for light detection was hardly able to efficiently detect light from a very small amount of sample. By contrast, the chip for light detection according to an embodiment has the reflecting section 12 at a position which is opposite to the direction D for fluorescence detection. Therefore, it causes fluorescence emitted in the direction opposite to the direction D for fluorescence detection to be reflected back to the direction D for fluorescence detection. As the result, it detects more fluorescence F than the chip in the related art and hence it is able to efficiently detect fluorescence F emitted from a very small amount of sample, thereby improving the accuracy of analysis.

Figure 4:
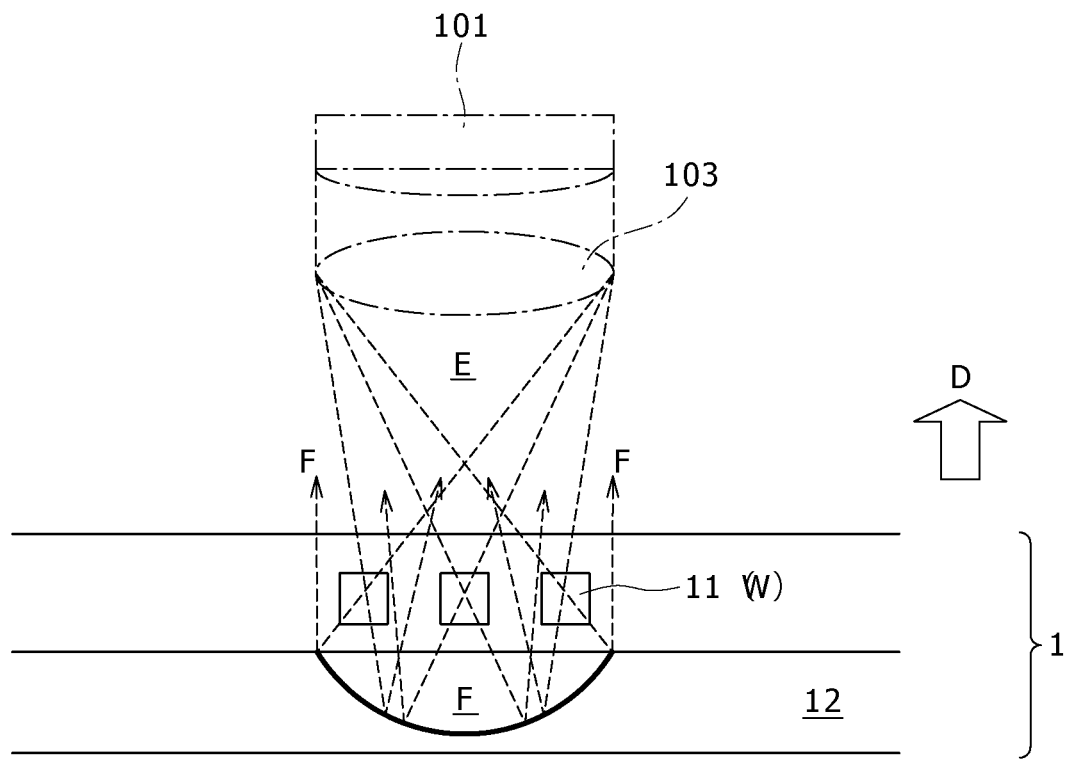
FIG. 4 is a schematic sectional view showing the light detecting chip according to the fourth embodiment.

As mentioned above, the chip 1 for light detection according to an embodiment has the light reflecting section 12, which is not specifically restricted in its structure so long as it is capable of reflecting fluorescence F emitted from the sample. For example, in the first and second embodiments shown in FIGS. 1 and 2, more than one light reflecting section 12 are arranged for more than one detection region 11, and in the fourth embodiment shown in FIG. 4, one light reflecting section 12 is arranged for one detection region 11.

Figure 5:
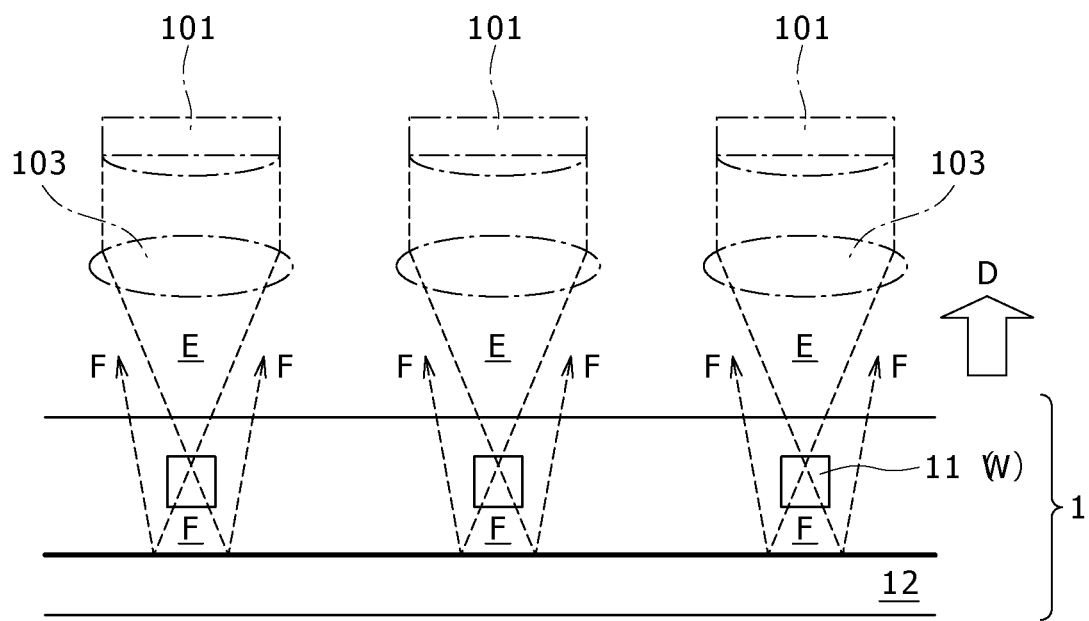
FIG. 5 is a schematic sectional view showing the light detecting chip according to the fifth embodiment.

As mentioned above, the chip 1 for light detection according to an embodiment has the light reflecting section 12, which is not specifically restricted in its shape so long as it is capable of reflecting fluorescence F emitted from the sample. It may be a spherical concave mirror which is used in the first and second embodiments shown in FIGS. 1 and 2, or an aspherical concave mirror which is used in the fourth embodiment shown in FIG. 4, or a plane mirror which is used in the fifth embodiment shown in FIG. 5.

Figure 6:
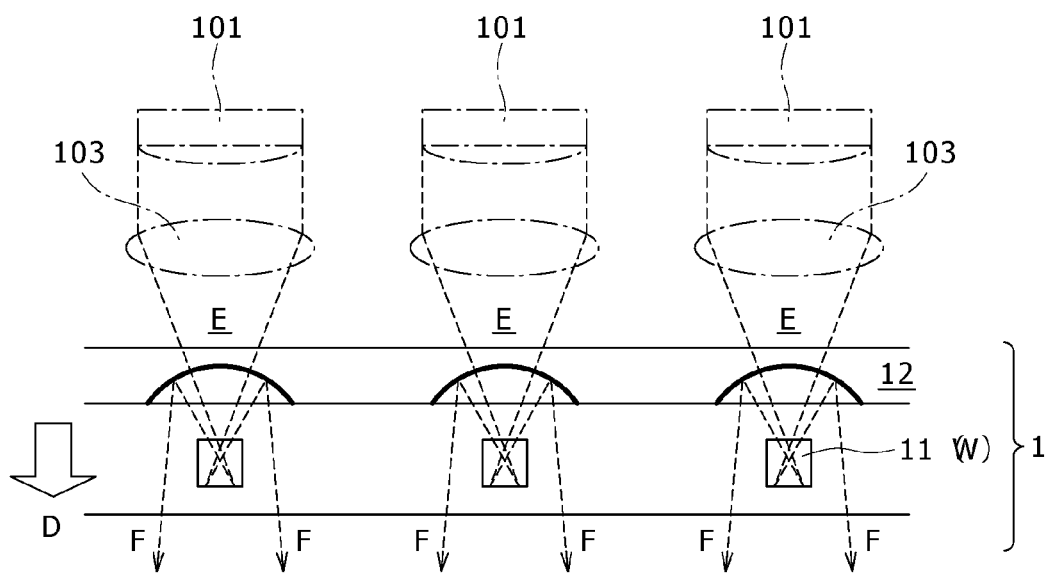
FIG. 6 is a schematic sectional view showing the light detecting chip according to the sixth embodiment.

The light detecting chip 1 according to an embodiment may have the light reflecting section 12 which transmits excitation light E directed to the sample but reflects the fluorescence F emitted from the sample. This light reflecting section 12 permits the direction of light irradiation and light detection to be reversed as in the sixth embodiment shown in FIG. 6. The light irradiation and light detection in the reverse direction through the detection region 11 makes it possible to freely arrange the light irradiating section 101 for irradiation and the light detecting section 102 to detect fluorescence (not shown).

(3) Light Transmission Controlling Section 13

The light transmission controlling section 13 blocks light (excitation light E) directed to the sample but transmits fluorescence F emitted from the sample. It is not essential for the light detecting chip 1 according to an embodiment; however, it will improve the S/N ratio.

Figure 7:
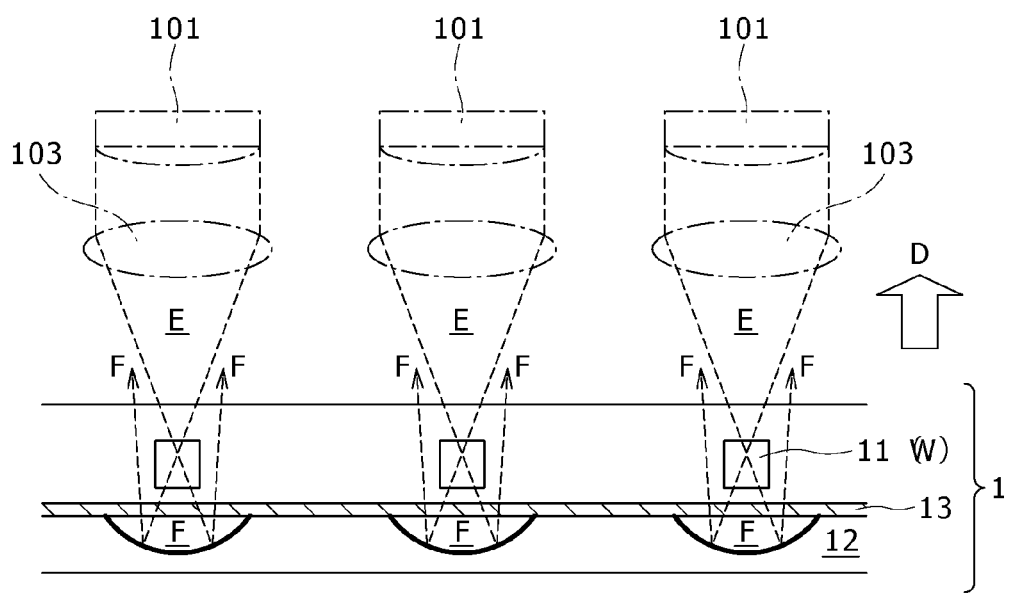
FIG. 7 is a schematic sectional view showing the light detecting chip according to the seventh embodiment.
Figure 8:
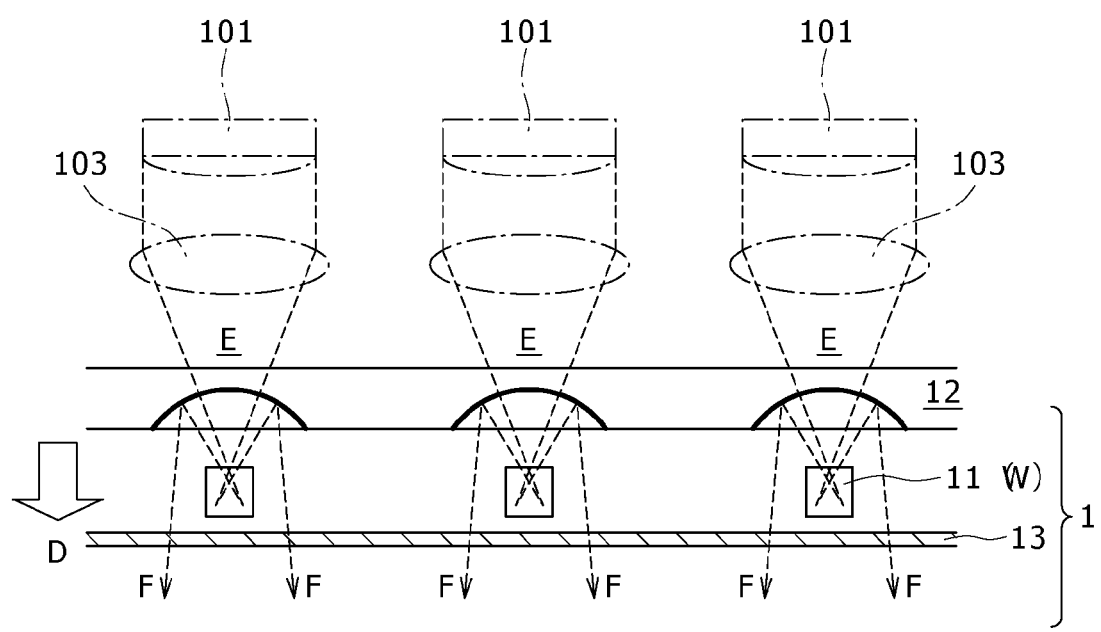
FIG. 8 is a schematic sectional view showing the light detecting chip according to the eighth embodiment.

The light transmission controlling section 13 may be placed between the detection region 11 and the light reflecting section 12, as in the seventh embodiment shown in FIG. 7, in which the light for irradiation and the light for detection are in the same direction. Also, it should preferably be placed at a position to which fluorescence is directed from the detection region 11, as in the eighth embodiment shown in FIG. 8, in which the light for irradiation and the light for detection are in the opposite direction through the detection region 11.

Thus, the light transmission controlling section 13 arranged described above prevents the excitation light E from scattering in the direction of fluorescence detection. The result is a decrease in noise due to the excitation light E and an improved S/N ratio.

2. Light Detecting Device 10

Figure 9:
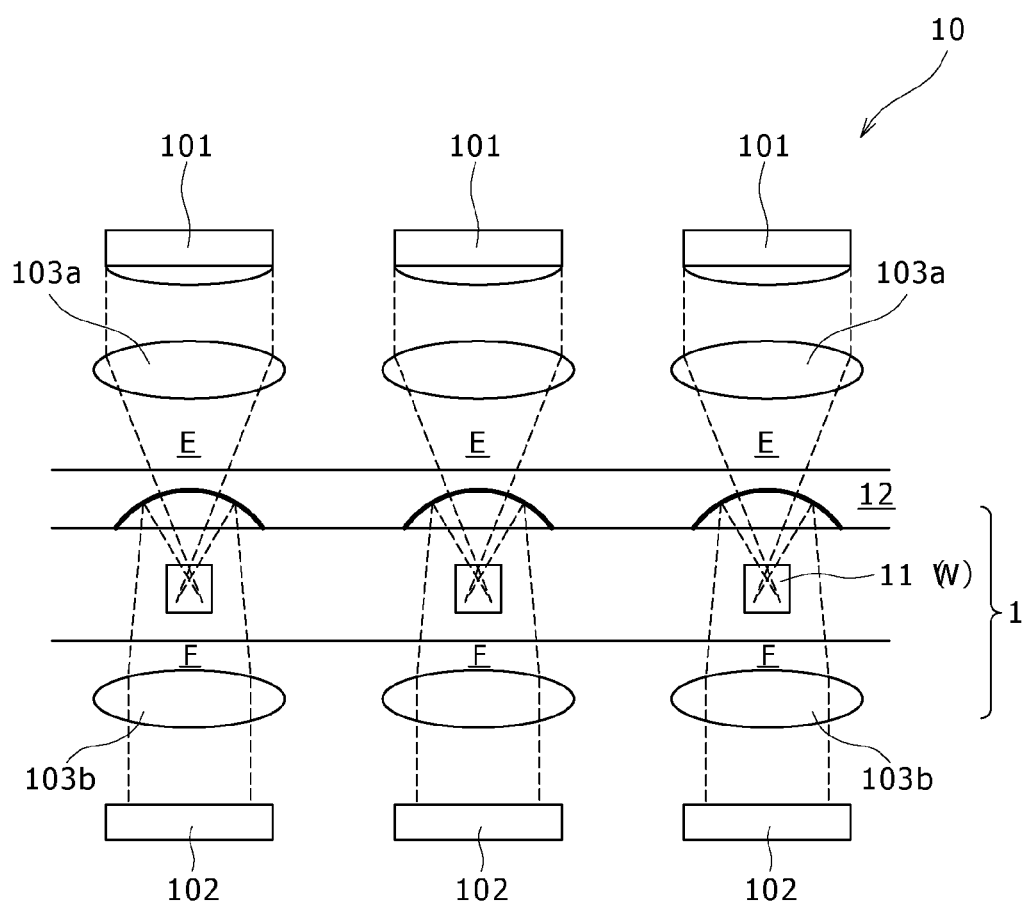
FIG. 9 is a schematic conceptual drawing showing the light detecting device according to the first embodiment.

FIG. 9 is a schematic conceptual drawing showing the light detecting device 10 according to the first embodiment. The light detecting device 10 is composed at least of (1) the light irradiating section 101, the detection region 11, and (2) the light detecting section 102, the light reflecting section. It may optionally have (3) the condenser lens 103, (4) the optical filter 104, (5) aperture 105, and the barrier, according to need. These components will be described below in more detail. Incidentally, the detection region 11 and the light detecting section 12 function in the same way as mentioned above for the light detecting chip 1. Therefore, their description is omitted hereunder.

(1) The Light Irradiating Section 101

The light irradiating section 101 is intended for irradiation to the sample with the excitation light E.

The light detecting device 10 according to an embodiment has the light irradiating section 101 which is placed anywhere without specific restrictions so long as it is capable of irradiating light to the sample. For example, in the first embodiment shown in FIG. 9, more than one light irradiating section 101 are arranged for individual detection regions 11. This arrangement permits the individual detection regions 11 to be irradiated with the excitation light E varying in wavelength so that various detections can be accomplished at the same time.

Another possible arrangement (not shown) is such that a plurality of detection regions 11 are scanned with one light irradiating section 101 or irradiated with the excitation light E.

In the light detecting device 10 according to an embodiment, the light irradiating section 101 can employ any known light irradiating method without specific restrictions. For example, light irradiation will be accomplished by using any of LED (light emitting diode), semiconductor laser, and EL illumination, alone or in combination.

If a plurality of light irradiating section 101 are arranged for the individual light detection regions 11, there are two ways of light irradiation. The first one is by simultaneous irradiation and simultaneous detection. This way saves time for data acquisition. The second one is by sequential irradiation and sequential detection. This way reduces noise from the juxtaposed light irradiating section 101.

(2) Light Detecting Section 102

The light detecting section 102 is intended for detection of fluorescence F emitted from the sample.

The light detecting device 10 according to an embodiment has the light detecting section 102, which is arranged in any way without specific restrictions so long as it is capable of detection of fluorescence F from the sample. For example, a plurality of light detecting section 102 may be arranged for individual detection regions 11 as in the first embodiment shown in FIG. 9. This arrangement permits simultaneous detection of fluorescence F emitted from the sample placed in each detection region 11.

Another possible arrangement (not shown) is such that a plurality of detection regions 11 are scanned with one light detecting section 102 or irradiated sequentially with the excitation light E. This arrangement permits detection of fluorescence F emitted from the sample placed in each detection region 11.

The light detecting device 10 according to an embodiment should preferably be constructed such that the light detecting section 102 is positioned opposite to the light irradiating section 101, with the detection region 11 interposed between them. This construction permits free arrangement of the light irradiating section 101 and the light detecting section 102.

The light detecting device 10 according to an embodiment may employ any known light detecting method without specific restrictions. These methods may use such areal imaging elements as PD (photodiode), CCD (charge coupled device), and CMOS (complementary metal oxide semiconductor), or a multichannel light detector which is composed of a plurality of light detectors arranged in an array.

(3) Condenser Lenses 103a and 103b

The first embodiment shown in FIG. 9 employs a plurality of condenser lenses 103a for excitation light, each of which is placed between the light irradiating section 101 and the light detection region 11, to condense light from the light irradiating section 101. The light detecting device 10 according to an embodiment does not essentially need the condenser lens 103a for excitation light. However, as in this embodiment, by providing the condenser lenses 103a, it directs light accurately to the sample placed in the detection region 11.

Moreover, this embodiment also employs a plurality of condenser lenses 103b, each of which is placed between the light detection region 11 and the light detecting section 102, to condense fluorescence F from the sample placed in the detection region 11 onto the light detecting section 102. The light detecting device 10 according to an embodiment does not essentially need the condenser lens 103b. However, as in this embodiment, by providing the condenser lenses 103b, it intensifies signals such as fluorescence F, thereby improving the S/N ratio.

(4) Optical Filters 104a and 104b

Figure 10:
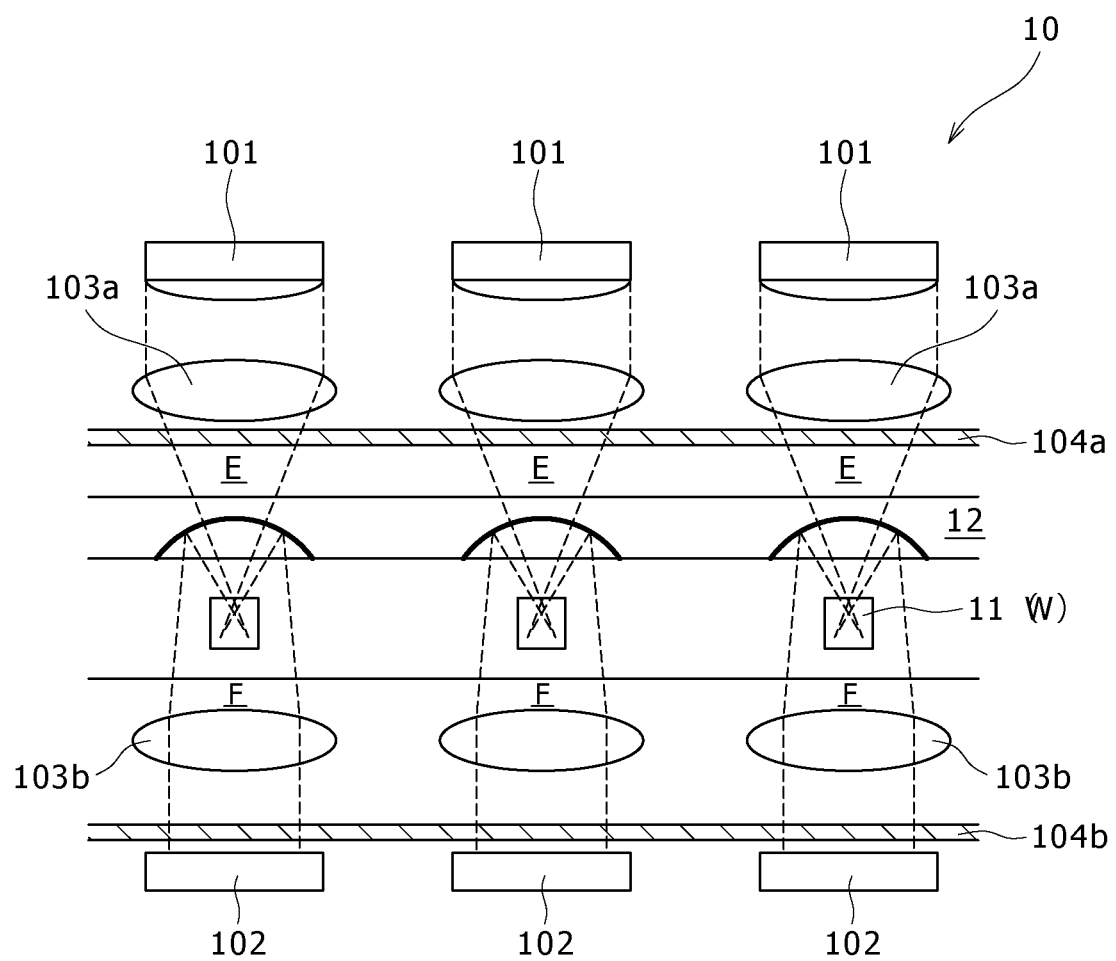
FIG. 10 is a schematic conceptual drawing showing the light detecting device according to the second embodiment.

FIG. 10 is a schematic conceptual drawing showing the light detecting device 10 according to the second embodiment. This embodiment employs the optical filters 104a for excitation light, each of which is placed between the light irradiating section 101 and the detection region 11. The light detecting device 10 according to an embodiment does not essentially need the optical filter 104a for excitation light. However, as in this embodiment, by providing the optical filters 104a, it permits each detection region 11 to be irradiated selectively with excitation light having a desired wavelength.

Moreover, this embodiment also employs the optical filter 104b for light reception which is placed between each detection region 11 and each light detecting section 102. The light detecting device 10 according to an embodiment does not essentially need the optical filter 104b for light reception. However, as in this embodiment, by providing the optical filters 104b, desired wavelength can be received selectively out of fluorescence F emitted from the sample placed in each detection region 11.

(5) Apertures 105a, 105b, Barrier

Figure 11:
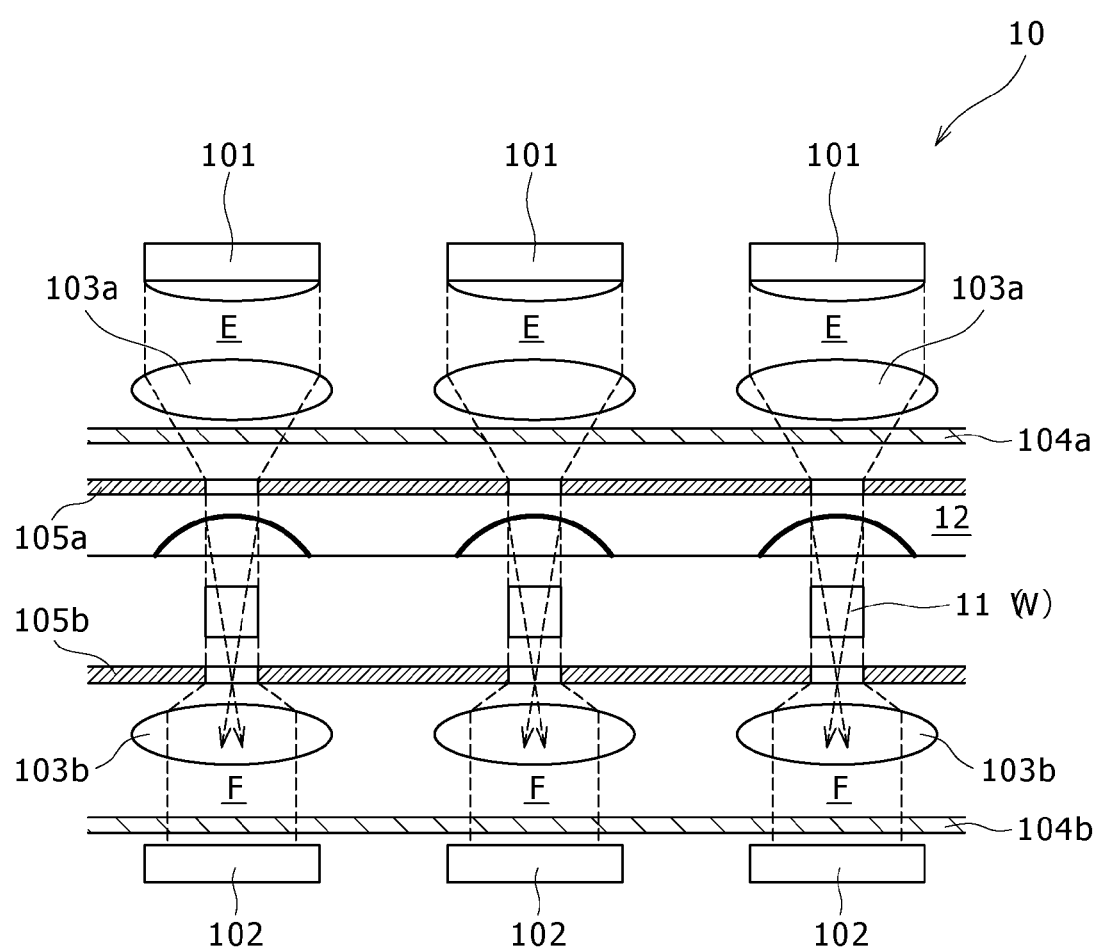
FIG. 11 is a schematic conceptual drawing showing the light detecting device according to the third embodiment.

FIG. 11 is a schematic conceptual drawing showing the light detecting device 10 according to the third embodiment. This embodiment employs the aperture 105a between each light irradiating section 101 and each detection region 11. The light detecting device 10 according to an embodiment does not essentially need the aperture 105a. However, as in this embodiment, it prevents light from each light irradiating mean 101 from irradiating other detection regions 11 (say, adjacent ones) than the corresponding one. This improves the S/N ratio.

Moreover, this embodiment also employs the aperture 105b between each detection region 11 and each light detecting section 102. The light detecting device 10 according to an embodiment does not essentially need the aperture 105b. However, as in this embodiment, it reduces crosstalk from other detection regions 11 (say, adjacent ones) than the corresponding one. This improves the S/N ratio.

The light detecting device 10 according to an embodiment may also employ, in addition to the apertures 105a and 105b, the barrier (not shown) between the lenses so as to produce the same effect as mentioned above.

The light detecting chip 1 and the light detecting device 10 provided with it according to an embodiment is capable of not only examining the physical properties of the substance contained in the sample placed in the detection region 11 but also quantitatively analyzing the substance contained in the sample by electrophoresis, with the detection region 11 placed in the channel C.

Such analysis may be accomplished by forming a liquid sample into a flow cell (composed of a sample and a sheath flow holding it therein) and acquiring, by means of the light detecting section 102, the intensity or image of fluorescence emitted from the substance flowing in the flow cell. The flow cell may be constructed in the same way as in the flow cytometry which is in actual use or under research and development. Detection of light from the sample flowing through the micro channel C makes it possible to sort fine particles, such as cells and nucleic acid, in the sample in the downstream of the channel according to the thus obtained information.

The present embodiments make it possible to efficiently detect light from a very small amount of light and is expected to improve the accuracy of analysis.

The technology mentioned above will contribute to improvement in analysis in various fields of medicine (pathology, tumor immunology, transplantation, genetics, regenerative medicine, and chemotherapy), innovative drug development, clinical laboratory test, food industry, agriculture, engineering, legal medicine, and criminal identification.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A light detecting chip comprising:
at least one detection region configured to receive excitation light from a light source and to accommodate a sample that is capable of emitting fluorescent light; and
a light reflecting section configured to reflect at least a portion of the fluorescent light emitted from the sample in a direction toward a light detector and at least partially back toward the detection region,
wherein the detection region is in a channel or a well, and is positioned between the light reflecting section and the light source.

2. The light detecting chip according to claim 1, further comprising a plurality of the detection regions placed in a channel and in a plurality of wells, the channel and wells being formed together in a substrate.

3. The light detecting chip according to claim 1, wherein the light reflecting section is selected from the group consisting of a spherical concave mirror, an aspherical concave mirror, or a planar mirror.

4. The light detecting chip according to claim 1, wherein the light reflecting section transmits at least a portion of excitation light that is directed to the sample from a light source.

5. The light detecting chip according to claim 1, further comprising a plurality of detections regions and a plurality of light reflecting sections, wherein each light reflecting section reflects at least a portion of the fluorescent light emitted from a plurality of samples associated with a plurality of the detection regions in the direction toward the light detector.

6. The light detecting chip according to claim 1, further comprising a light transmission controlling section for blocking at least a portion of the excitation light that is directed to the sample from the light source from scattering in the direction toward the light detector.

7. The light detecting chip according to claim 6, wherein the light transmission controlling section is positioned between the detection region and the light reflecting section, and is in a position where the fluorescent light is directed from the detection region.

8. A light detecting device comprising:
a light source configured to emit excitation light;
at least one detection region configured to accommodate a sample capable of emitting fluorescent light;
a light reflecting section configured to reflect at least a portion of the fluorescent light emitted from the sample in a direction toward a light detector and at least partially back toward the detection region; and a light detection section configured to receive at least a portion of the fluorescent light that is reflected by the light reflecting section, wherein the detection region is in a channel or a well, and is positioned between the light reflecting section and the light source.

9. The light detecting device according to claim 8, further comprising a plurality of the detection regions placed in a channel and in a plurality of wells, the channel and wells being formed together in a substrate.

10. The light detecting device according to claim 8, wherein the light reflecting section is selected from the group consisting of a spherical concave mirror, an aspherical concave mirror, or a planar mirror.

11. The light detecting device according to claim 8, wherein the light reflecting section transmits at least a portion of excitation light that is directed to the sample from a light source.

12. The light detecting device according to claim 8, further comprising a plurality of detections regions and a plurality of light reflecting sections, wherein each light reflecting section reflects at least a portion of the fluorescent light emitted from a plurality of samples associated with a plurality of the detection regions in the direction toward the light detector.

13. The light detecting device according to claim 8, wherein at least one optical filter is placed between the light source and the detection region and is configured to filter at least a portion of the excitation light.

14. The light detecting device according to claim 8, wherein the detection region is positioned between the light reflecting section and the light detection section.

15. The light detecting device according to claim 8, wherein the light reflecting section is positioned between the light source and the detection region.

16. The light detecting device according to claim 8, further comprising at least one condenser lens for condensing at least a portion the excitation light.

17. The light detecting device according to claim 8, further comprising a first aperture positioned between the light source and the detection region, and a second aperture positioned between the detection region and the light detection section.

18. The light detecting device according to claim 8, further comprising a light transmission controlling section for blocking at least a portion of excitation light that is directed to the sample from a light source from scattering in the direction toward the light detector.

19. The light detecting device according to claim 18, wherein the light transmission controlling section is positioned between the detection region and the light reflecting section, and is in a position where the fluorescent light is directed from the detection region.

* * * * *